United States Patent [19]

Barsaloux

[11] 4,215,580
[45] Aug. 5, 1980

[54] FLUID SAMPLING APPARATUS

[76] Inventor: Reginald G. Barsaloux, 93 Lynndale Rd., Simcoe, Ontario, Canada, N3Y 4W9

[21] Appl. No.: 43,590

[22] Filed: May 29, 1979

[51] Int. Cl.² ............................................. G01N 1/12
[52] U.S. Cl. .............................................. 73/425.4 R
[58] Field of Search .................... 73/425.4 R; 215/355

[56] References Cited

U.S. PATENT DOCUMENTS

| 3,598,183 | 5/1952 | Long et al. ........................ 73/425.4 |
| 4,090,630 | 5/1978 | Wiedmer ............................. 215/355 |

FOREIGN PATENT DOCUMENTS 596600  1/1948  United Kingdom ............... 73/425.4 R

*Primary Examiner*—S. Clement Swisher
*Attorney, Agent, or Firm*—McCarthy & McCarthy

[57] ABSTRACT

A fluid sampling apparatus for taking samples of fluid from predetermined depths in a body of water comprises a receptacle for releasably holding therein a sample collection bottle. A single suspension means such as a rope is provided, by means of which the assembly can be raised and lowered. Attached to the bottom of the suspension means is an interference fit stopper such as a cork and a resilient engaging means, for releasably engaging ribs on the neck of a bottle disposed within the receptacle. As the assembly is lowered by means of the suspension means, it is suspended by means of the resilient releasable means engaging against ribs on the bottle neck. When it has been lowered to the required depth, the suspension means is jerked suddenly upwardly, causing the resilient releasable means to release the bottle, with consequent removal of the stopper to permit filling of the bottle. After freeing from the bottle, the resilient engaging means abuts against the top wall of the container, allowing the assembly to be withdrawn upwardly by means of the suspension means.

10 Claims, 4 Drawing Figures

FLUID SAMPLING APPARATUS

FIELD OF THE INVENTION

This invention relates to fluid sampling apparatus and systems, and more particularly to a sampling apparatus for taking a sample of a liquid from a known depth within a body of such liquid.

BACKGROUND OF THE INVENTION

The need to take liquid samples from depths within a body of such liquids occurs in a number of contexts. For example, it is often necessary to withdraw a sample of oil from a known depth within an oil storage tank, so as to analyse its composition. Similarly, in checking on water quality in inland lakes and streams, analysis of water samples from known depths may be required. Also in industrial waste disposal processes which require the use of settling tanks and ponds, monitoring of progress of the process requires the extraction of liquid samples from known depths. There is thus a need for an apparatus which is simple yet efficient in use, for collection of such samples.

The lowering of a simple container to the required depth and collection of liquid therein is the simplest means, provided that one can be sure that all of the liquid collected therein comes from the required depth. In order to accomplish this, the container should preferably remain closed until the predetermined depth is reached, and then opened at that depth for filling purposes. Then it must be withdrawn to the surface without spillage and refilling thereof with liquid from another depth level. It is also desirable to be able to collect a sample of known, predetermined size in a convenient form of container for subsequent laboratory analysis.

SUMMARY OF THE INVENTION

It is an object of the present invention to provide a novel means for liquid sample collection from a known, predetermined depth in a body of liquid.

The present invention provides a receptacle within which a sample collection container such as a corked bottle can be releasably held. The receptacle and container therein can be suspended, lowered and raised through the body of liquid by means of a suspension means such as a rope bearing graduations to indicate depth. The suspension means is attached at one end to both the bottle stopper, e.g. the cork, and to a resilient means for releasably engaging formations on the bottle neck. The container and bottle are lowered on the rope with the cork stoppering the bottle and the weight of the assembly supported by the engagement of the bottle neck formations with the resilient means on the end of the rope. When the rope with the assembly thereon has been lowered to the required depth, a sudden upward jerk on the rope causes the resilient means to free from the neck formations and consequently the cork to be removed from the bottle, permitting the bottle to be filled with liquid at that depth. The resilient means and cork remain on the end of the rope, and engage against other structural formations of the container, when removed from engagement with the bottle, so that the container remains suspendible by the rope and can be raised by the rope.

BRIEF REFERENCE TO THE DRAWINGS

DESCRIPTION OF THE PREFERRED EMBODIMENTS

Preferably, the receptacle has a top wall disposed above the side wall, and the suspension means passes downwardly through an aperture in the top wall, the engagement means and stopper being too large to pass upwardly through the aperture. By this means, the receptacle and the container therein remain suspendable by the suspension means even when the stopper is removed from the container. It is also preferred that the weighted base be generally circular and the side wall be generally cylindrical. The restraining means are suitably protrusions extending generally radially inwardly from the upper part of the side wall, to engage the container shoulder. This shape and arrangement conveniently fits the standard shaped generally cylindrical laboratory sample bottle. It also conveniently accommodates situations where the sample is to be withdrawn from a cylindrical pipe, e.g. a sample withdrawal pipe commonly found extending downwardly into an oil storage tank for this purpose.

The preferred arrangement of the present invention is for the container to be removable from the side of the receptacle, rather than axially. This greatly simplifies construction of the upper end of the receptacle and its suspension by the suspension means. For this purpose, it is preferred to have a front opening in the generally cylindrical side wall, along with a closure means, permitting withdrawal of the container from the space therein forwardly through the front opening, upon opening of the closure means. Suitably, the side wall is split axially from the top of the front opening to the top edge thereof, so that the side wall is circumferentially expandable and contractable between a container withdrawal position and a container restraining position, the closure means holding the side wall in its circumferentially contracted position when closed, to hold the container therein.

DETAILED DESCRIPTION OF THE SPECIFIC PREFERRED EMBODIMENTS

Figure 1:
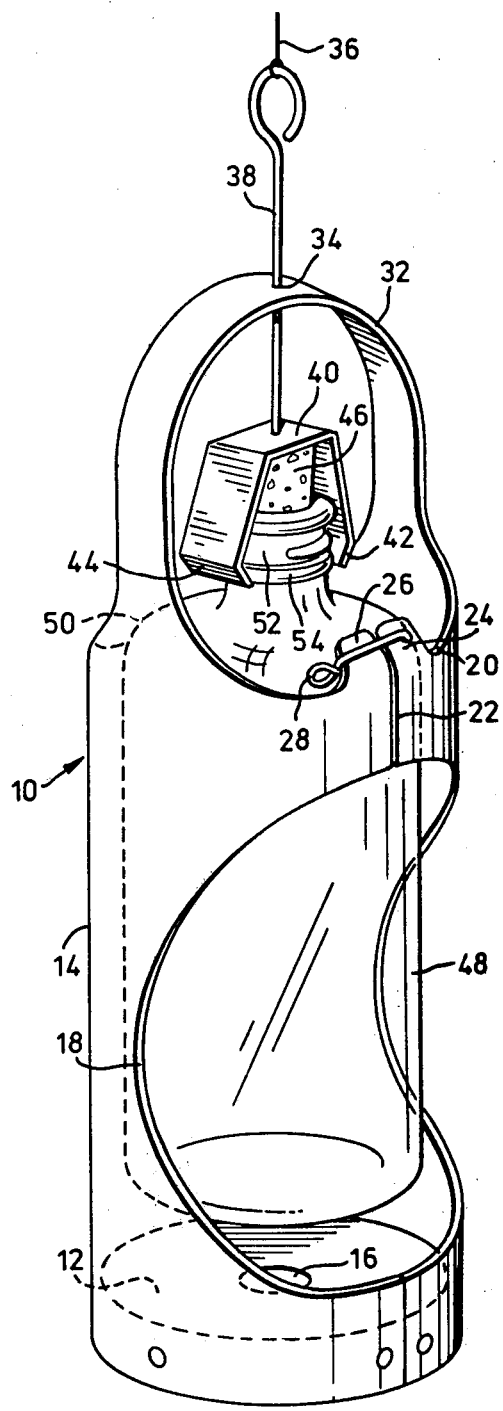
FIG. 1 is a perspective view of a container receptacle of the present invention, with a container, namely a bottle, fitted therein.

In the drawings, in which like reference numerals indicate like parts, and specifically with reference to FIG. 1, a receptacle 10 according to the invention has a lower, circular weighted base 12, to which is attached by flush rivets a generally cylindrical upstanding side wall 14. The base 12, which is conveniently of lead or other heavy substance to assist in sinking the receptacle in use, has a central drain hole 16 extending therethrough to facilitate raising of the receptacle within a body of liquid. The side wall 14 is suitably of aluminum.

The side wall 14 has a front cutaway portion 18 with a curved periphery extending from adjacent the base 12 to close to the upper edge 20 of the front part of the side wall. The side wall is split at 22 from the top of the cutaway portion 18 to the upper edge 20 at the front part. At opposed sides of the split 22, restraining means in the form of inwardly extending protrusions 24, 26 are provided, secured together in close relationship by a removable clasp 28, pivotted in the protrusion 24 and received in a notch 30 (FIG. 4) of the protrusion 26. Other inwardly extending protrusions (not shown) are provided at the upper edge of the side wall 14 diametrically opposed to the protrusions 24, 26.

The receptacle 10 has an integral top wall 32 in the form of a relatively narrow band, extending upwardly in semicircular fashion above the upper edge 20. An aperture 34 is provided at the uppermost central part of the top wall 32. The receptacle 10 has a suspension means in the form of a rope 36 and hooked rigid rod 38 secured to the bottom end of the rope 36. The rod passes downwardly through the aperture 34 in the top wall 32, and has secured to its lower end, below the top wall 32, a spring steel strip 40, of generally inverted U-shape, the arms of which have lower inwardly extending projections 42, 44. Also attached to the lower end of the rod 38, beneath the strip 40 and embraced by the arms thereof, is an interference fit stopper 46, namely a cork, for the bottle container 48 as shown.

The base 12 and side wall 14 thus define within them a container-receiving space, which in practice contains a sample receiving bottle 48, of generally conventional form, having shoulders 50, a narrow neck 52 and an annular projection 54 on the neck, normally for sealing engagement with a screw threaded cap for the bottle. The bottle 48 is retained against upward removal from within the receptacle 10 by engagement of the inwardly extending projections 24, 26 against the shoulder 50 the bottle. A degree of axial movement of the bottle within the container receiving space, e.g. about 1 inch, is however provided.

Figures 2, 3:
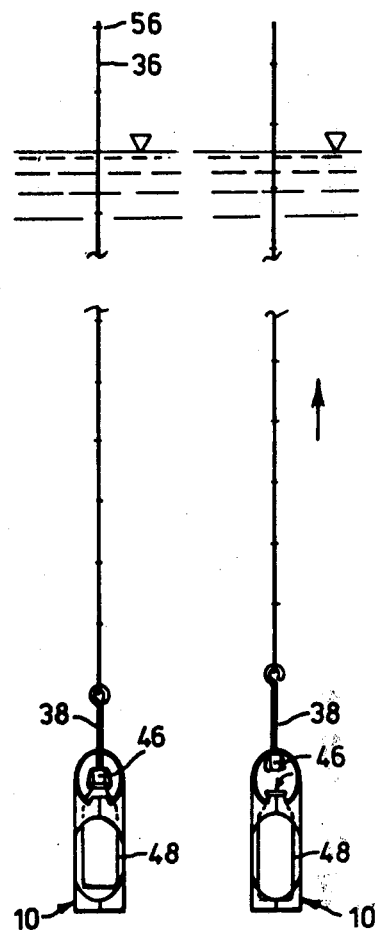
FIG. 2 is a view, on the smaller scale, of the receptacle and container lowered to a predetermined depth in a body of liquid.
FIG. 3 is a view similar to FIG. 2, but showing the bottle unstoppered but held within the receptacle below the liquid surface for filling with liquid at the predetermined depth.

In operation, the stopper 46 is interference fitted into the neck of the empty bottle 48 received within the container receiving space, and upon so doing, the projections 42, 44 of the spring steel strip 40 engage under the projecting rib 54 on the neck of the bottle. This engagement is sufficiently tight that the entire assembly, namely the receptacle 10 and the bottle 48, can now be suspended by means of the rope 36 and rod 38, provided that no sudden upward jerking motion is exerted on the rope 36 which might cause the projections 42, 44 to come out of contact with the rib 54. In this manner, the assembly can be lowered to a known depth within a body of water, as diagramatically illustrated in FIG. 2. The rope 36 is conveniently graduated by markers 56 to indicate to the user the depth of the sample bottle 48 within the body of liquid. When the assembly has been lowered to the required depth, a sudden, upward jerking movement is exerted on the rope 36. As shown in FIG. 3, this causes the projections 42, 44 of the spring steel strip 40 to come out of engagement with rib 54, and consequently to cause cork 46 to come out of the neck 52 of the bottle 48. The upward force is in fact exerted by the shoulder 50 of the bottle against the inwardly extending projections 24, 26 on the receptacle 10, by means of which engagement, until now, the bottle and receptacle have been suspended together from the rope 36.

When, as a result of the jerking upward movement, the projections 42, 44 leave engagement with the rib 54 and cork 46 leaves the bottle neck, the bottle moves axially downwardly relative to the container 10 to rest upon the base 12 within the container receiving space, and the spring strip 40 and cork 46 rise axially to engage against the underside of the top wall 32. This is the position illustrated in FIG. 3. The user can sense this movement, and knows the bottle has properly opened. Now, the sample bottle 48 can fill with liquid from the prescribed depth. By means of the relative movement of the bottle away from the stopper, previously described, sufficient clearance is left to permit ready filling of the bottle without interference from the stopper.

Figure 4:
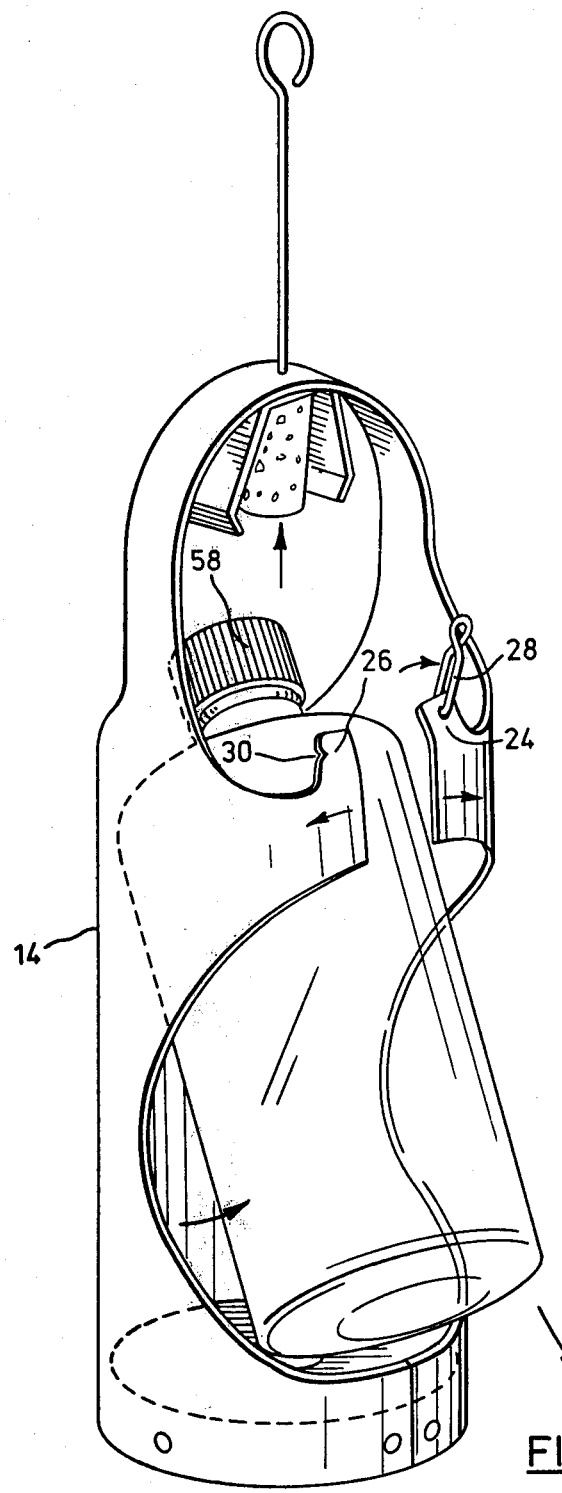
FIG. 4 is a view similar to that of FIG. 1, showing the bottle being removed from the receptacle.

Once the bottle is filled, the assembly can be withdrawn upwardly through the body of liquid, since it remains suspended by the rope 36, due to engagement of the spring strip 40 on the end of the rod 38 with the underside of the top wall 32, and the retention of the bottle within the container receiving space in the receptacle 10. Since the bottle is already full, it will not pick up any significant amounts of liquid from other depths, as it is raised. Once it is removed above the surface of the liquid, a conventional screw thread stopper 58 can be fitted in sealing engagement on the neck of the bottle. To remove the sample bottle from the container, the clasp 28 is moved out of notch 30 on protrusion 26, by squeezing the two portions of the side wall 14 together across split 22, and the clasp is then pivotted as shown in FIG. 4, out of engagement with protrusion 26. Then the two halves of the side wall 14 can be separated across the split 22, to permit forward removal of the bottle from the receptacle 10 through the forward aperture 18. The upper portion of the receptacle 10 does not therefore need to be dissemblable to permit axial withdrawal of the bottle, thereby greatly simplifying the structure of the upper portion of the receptacle 10.

It will be observed that the receptacle is of overall cylindrical shape, and that the top wall 32 thereof lies within the axial cylindrical projection of the receptacle as a whole. Moreover the top wall is part circular, thereby permitting the receptacle and the bottle contained therein to be withdrawn easily and smoothly upwardly through a body of liquid, even through a narrow sample pipe as commonly encountered in an oil storage tank.

The apparatus according to the invention is thus simple and easy to use, and economical to manufacture and assemble. The side wall structure can be made from a single piece of aluminum, readily assembled; standard laboratory size sample bottles can be used. The apparatus can be made in a variety of different sizes as required.

Whilst a specific embodiment of the invention has been described and illustrated herein in detail, this is not to be construed as limiting. The scope of the invention is limited only by the scope of the appended claims.

I claim:

1. A receptacle for releasable reception therein of an interference fit stoppered type container,
    said receptacle comprising:
    a weighted base and side wall extending upwardly therefrom to define a container-receiving space, said side wall having a front opening therein and closure means, permitting withdrawal of a container from the container-receiving space forwardly through said front opening upon opening of said closure means, and the container being checked against such withdrawal when the closure means is closed;

restraining means on said receptacle adapted to engage the container and restrict movement of the container away from said weighted base when within the container-receiving space;

suspension means extending upwardly from the receptacle;

an interference fit stopper for said container and resilient engagement means associated with the stopper, secured to a lower end of said suspension means, for resiliently releasably engaging the container when the stopper is fitted to the container and preventing removal of the stopper therefrom;

the resilient engagement means being releasable from engagement with the container, and the stopper consequently being removed from the container, upon upward jerking force applied to the suspension means;

the receptacle being suspendable by said suspension means whether or not the resilient engagement means and the stopper are in engagement with the container.

2. The receptacle according to claim 1 including a top wall disposed above the side wall, the suspension means passing downwardly through an aperture in the top wall, the engagement means and stopper being too large to pass upwardly through said aperture.

3. The receptacle according to claim 2 wherein said weighted base is generally circular and said side wall is generally cylindrical, the said restraining means comprising protrusions extending generally radially inwardly from the upper part of the side wall to engage the container shoulder.

4. The receptacle of claim 3 wherein the side wall is split axially from the top of the front opening to the upper edge thereof, the side wall thus being circumferentially expandable and contractable between a container withdrawal position and a container restraining position, said closure means holding the side wall in a circumferentially contracted position when closed.

5. The receptacle of claim 4 wherein some of said inwardly extending protrusions comprise integral formations of the side wall on opposed sides of said axial split, and the closure means comprises a clasp extending from one to the other of said protrusions across the split, when the closure means is closed.

6. The receptacle of claim 5 wherein the weighted base includes a drainage hole therethrough.

7. The receptacle of claim 6 wherein the engagement means comprises a generally inverted U-shaped formation, the downward extremities of the arms thereof having inwardly projecting portions to releasably engage a container formation therebetween, and the stopper being disposed between said arms and extending from the base of the U-shaped formation.

8. The receptacle of claim 6 wherein the axial extent of the container receiving space, defined between the weighted base and the inwardly extending protrusions, permits limited axial movement of the container therein.

9. The receptacle of claim 4 wherein the top wall is arcuately curved upwardly across the top thereof, and disposed within the cylindrical axial projection of the side wall thereof.

10. In combination, a receptacle as claimed in claim 4 and a container in the form of a bottle having a narrow upper neck, cork-receiving aperture at the top of said neck and shoulders below the neck thereof, said shoulders being engageable against the inwardly extending protrusions at the upper part of said side wall to prevent axial withdrawal of the bottle from the container, and the resilient engagement means engaging outwardly extending ribs on the neck of the bottle, the axial distance between the weighted base and the inwardly extending protrusions of the container being greater than the axial length of the bottle from base to shoulder, to permit limited axial movement of the bottle within the receptacle.

* * * * *